United States Patent [19]

Schneider et al.

[11] Patent Number: 5,445,813
[45] Date of Patent: Aug. 29, 1995

[54] STABLE MICROBUBBLE SUSPENSIONS AS ENHANCEMENT AGENTS FOR ULTRASOUND ECHOGRAPHY

[75] Inventors: Michel Schneider, Troinex, Switzerland; Jean Brochot, Feigeres; Jérôme Puginier, Le Chable-Beaumont, both of France; Feng Yan, Meyrin/Geneva, Switzerland

[73] Assignee: Bracco International B.V., Amsterdam, Netherlands

[21] Appl. No.: 134,671

[22] Filed: Oct. 12, 1993

[30] Foreign Application Priority Data

Nov. 2, 1992 [EP] European Pat. Off. ............ 92810837

[51] Int. Cl.6 ............................................. A61K 49/00
[52] U.S. Cl. .................................. 424/9.51; 424/450; 424/9.52
[58] Field of Search .................... 424/9; 128/662.02

[56] References Cited

U.S. PATENT DOCUMENTS 4,684,479 8/1987 D'Arrigo ........................ 252/307
4,957,656 9/1990 Cerny et al. ..................... 252/311
5,271,928 12/1993 Schneider et al. ..................... 424/9

FOREIGN PATENT DOCUMENTS

WO91/09629 7/1991 WIPO .
WO91/15244 10/1991 WIPO .
WO92/11873 7/1992 WIPO .

*Primary Examiner*—Gary E. Hollinden
*Assistant Examiner*—Mary C. Cebulak
*Attorney, Agent, or Firm*—Nixon & Vanderhye

[57] ABSTRACT

Disclosed are injectable suspensions of gas filled microbubbles in an aqueous carrier liquid usable as contrast agents in ultrasonic echography. The suspensions comprise amphipathic compounds of which at least one may be a laminarized phospholipid as a stabiliser of the microbubbles against collapse with time and pressure. The concentration of phospholipids in the carrier liquid is below 0.01% wt but is at least equal to or above that at which phospholipid molecules are present solely at the gas microbubble-liquid interface. Also disclosed is a method of preparation of the stable suspensions of air or gas filled microbubbles.

12 Claims, 1 Drawing Sheet

//5,445,813

STABLE MICROBUBBLE SUSPENSIONS AS ENHANCEMENT AGENTS FOR ULTRASOUND ECHOGRAPHY

TECHNICAL FIELD

The invention relates to injectable suspensions of gas filled lo microbubbles in an aqueous carrier comprising amphipathic compounds of which at least one is a phospholipid stabilizer of the microbubbles against collapse with time and pressure. The phospholipid stabilizer may be in a lamellar or laminar form. The invention also comprises a method of making stable suspensions of microbubbles usable as contrast agents in ultrasonic echography.

BACKGROUND OF INVENTION

Use of suspensions of gas microbubbles in a carrier liquid as efficient ultrasound reflectors is well known in the art. The development of microbubble suspensions as echopharmaceuticals for enhancement of ultrasound imaging followed early observations that rapid intravenous injections can cause solubilized gases to come out of solution forming bubbles. Due to their substantial difference in acoustic impedance relative to blood, these intravascular gas bubbles are found to be excellent reflectors of ultrasound. Injecting into the blood-stream of living organisms suspensions of gas microbubbles in a carrier liquid strongly reinforces ultrasonic echography imaging, thus enhancing the visualisation of internal organs. Since imaging of organs and deep seated tissue can be crucial in establishing medical diagnosis a lot of effort is devoted to the development of stable suspensions of highly concentrated gas microbubbles which at the same time would be simple to prepare and administer, would contain a minimum of inactive species, would be capable of long storage and simple distribution. Many attempts towards a solution which will satisfy these criteria have been made, however, none have provided a completely satisfactory result.

It has been known from EP-A-0 077 752 (Schering) that suspensions of gas microbubbles can be made by mixing an aqueous solution of a surfactant with a solution of a viscosity enhancer as a stabilizer. The gas bubbles are introduced into the mixture by forcing the mixture of reagents and air through a small aperture. A suspension of $CO_2$ microbubbles may be obtained by addition of an acid to a mixture obtained from a solution containing a surfactant and sodium bicarbonate and a solution of the viscosity enhancer. Mixing the components however, is to be carried out just before use and the solution is to be consumed/injected immediately upon preparation. The disclosed surfactants (tensides) comprise lecithins; esters and ethers of fatty acids and fatty alcohols with polyoxyethylene and polyoxyethylated polyols like sorbitol, glycols and glycerol, cholesterol; and polyoxy-ethylene-polyoxypropylene polymers. Disclosed concentration of tensides in the suspension is between 0.01% and 10% wt and a preferred range is claimed to be between 0.5% to 5%. The viscosity enhancing and stabilizing compounds include for instance mono- and polysaccharides (glucose, lactose, sucrose, dextran, sorbitol); polyols, e.g. glycerol, polyglycols; and polypeptides like proteins, gelatin, oxypolygelatin, plasma protein and the like. The total amount of viscosity enhancing agent is limited to 0.5 and 50%. Use of polyoxypropylenepolyoxyethylene polymers (eg. Pluronic® F-68) as viscosity enhancing agent has also been disclosed. In the preferred example, equivalent volumes of tenside, a 0.5% by weight aqueous solution of Pluronic® F-68 (a polyoxypropylene-polyoxyethylene copolymer), and the viscosity enhancer (a 10% lactose solution) are vigorously shaken together under sterile conditions to provide a suspension of microbubbles. The suspension obtained lasted over 2 minutes and contained close to 50% of bubbles with a size below 50 $\mu$m. According to the document up to 50% of surfactants and/or viscosity enhancing agents may be employed, however, specific examples use between 1% and 4% of Pluronic® F-68.

Easy-to-produce aqueous suspensions usable as imaging agents in ultrasonic echography are disclosed in WO-91/15244 (Schneider et. al.). The suspensions contain film forming surfactants in laminar and/or lameliar form and, optionally, hydrophilic stabilizers. The laminarized surfactants can be in the form of liposomes i.e. microscopic vesicles, generally spherically shaped. These vesicles are usually formed of one or more concentrically arranged bi-molecular layers of amphipathic compounds i.e. compounds with a hydrophilic and a hydrophobic moieties. The molecules in the bilayers are organised so that the hydrophobic moieties are in facing relationship, the hydrophilic moieties pointing toward the water phase. The suspensions are obtained by exposing the laminarized surfactants to air or a gas prior to or after admixing with an aqueous phase. Conversion of film forming surfactants into lameliar form is carried out according to various liposome forming techniques including high pressure homogenisation or sonication under acoustic or ultrasonic frequencies. The concentration of phospholipids claimed is between 0.01% and 20% and the concentration of microbubbles is between $10^8$ and $10^9$ bubbles/ml. The microbubble suspensions remained stable for months. The concentration of phospholipids in Example 1 is 0.5%.

An attempt toward a stable echogenic suspension is disclosed in WO-92/11873 (Beller et. al.). Aqueous preparations designed to absorb and stabilise microbubbles for use as an echographic contrasting agent are made with polyoxyethylene/polyoxypropylene polymers and negatively charged phospholipids such as phosphatidylglycerol, phosphatidylinositol, phosphatidylethanolamine, phosphatidylserine as well as their lysoforms. The concentration range of phospholipids in the preparations may be between 0.0 1% and 5% by volume or weight, however, preparations with 1% of dipalmitoylphosphatidyl glycerol (DPPG) are specifically disclosed and claimed. In addition to the negatively charged phospholipids the compositions must contain between 0.1% and 10% of polymeric material (Pluronic® F-68). The total amount of solutes in the preparations is between 5.1% and 10.4%. The concentration of the microbubbles is not reported, however, according to the results given it may be estimated to be about $10^7$ bubbles/ml. The stability of the suspensions is reported to be better than that of EP-A-0 077 752.

Although the prior art compositions have merit, they still suffer several drawbacks which hamper their practical use. Firstly, some prior art compositions have relatively short life spans and secondly, they have a relatively low initial bubble count e.g. between $10^4$ and $10^5$ bubbles/ml. This makes reproducibility and analysis of echographic tests made with such compositions fairly difficult. In addition, some techniques produce bubbles in a wide range of diameters (up to 50 $\mu$m) which prevents their use as echographic agents in certain applications (e.g. echography of the left heart).

The need for stable formulations of microbubbles which will resist pressure variations in the blood streams and have a good shelf life is further amplified by poor stability of some of the state-of-the-art compositions. Microbubble formulations whose distribution and storage would not present problems are particularly important.

Another drawback is that many of the heretofore known compositions contain a high amount of different solutes such as polymers, phospholipids, electrolytes, and other which render their practical use more and more difficult. For example, it is known that use of polyoxyethylene/polyoxypropylene polymers (Pluronic ®) with particular patients may cause unpleasant side effects (see for instance G. M. Vercellotti et. al. Blood (1982) 59, 1299). Preparations with a high phospholipid content in certain cases may also be undesirable. In any event, compositions with a high degree of various solutes are administered reluctantly and their wide spread use is becoming considered to be undesirable. In fact, the trend in the pharmaceutical industry is to reduce concentrations of active and inactive ingredients in various medical or pharmaceutical formulations to their lowest possible levels and eliminate from the preparations everything that is not necessary. Finding alternative methods and formulating more effective compositions continues to be important. This is particularly so with microbubble suspensions used in echography since here the ingredients have no curative effect and should lead to the least possible after consequences. However, as stated above, the state of the art preparations with typical concentrations in the range of 1% and 4% by weight and the teachings of prior art discourage use of reduced amounts of phospholipids and other non-phospholipid additives. The reason for the discouragement is most probably hidden in the fact that in the course of the routine experimentation further reduction in concentration of the ingredients never produced suspensions which were stable enough to have any practical use or encourage further tinkering in the lower end of the known range.

SUMMARY OF THE INVENTION

The present invention is based on the unexpected finding lo that very stable suspensions of a gas filled microbubbles comprising at least $10^7$ microbubbles per millilitre may be obtained using phospholipids as stabilizers even if very low concentrations thereof are employed. The suspensions usable as contrasting agents in ultrasonic echography are obtained by suspending in an aqueous carrier at least one phospholipid as a stabiliser of the microbubbles against collapse with time and pressure, the concentration of the phospholipids being below 0.01% wt. but equal to or higher than that at which the phospholipid molecules are present solely at the gas microbubble-liquid interface.

It was quite unexpected to discover that as negligible amounts of the phospholipid surfactants involved here (used alone or with a relatively small proportions of other amphiphiles) can so effectively stabilize microbubbles. It is postulated that, in the presence of other amphipathic compounds (such as Pluronic ®) the mutual cohesion between stabilizer molecules is decreased and formation of monomolecular phospholipid films is inhibited. However, in the absence of large amounts of other amphiphilic agents, the unhindered intermolecular binding forces (electrostatic interaction or hydrogen bonding) between phospholipid molecules are sufficient to ensure formation of stable film-like structures stabilizing the bubbles against collapse or coalescence.

According to the invention, suspensions of high microbubble concentration, high stability, long storage capacity and ease of preparation may be obtained even if the concentrations of surfactants and other additives in the suspensions are kept well below the levels used in the state-of-the-art formulations. The amount of phospholipids used in the compositions of the invention may be as low as about that only necessary for formation of a single monolayer of the surfactant around the gas microbubbles while the concentration of the bubbles in the suspension is maintained above $10^7$ microbubbles per millilitre. In the present invention, microbubbles with a liposome-like double layer of surfactant (gas filled liposomes) are not likely to exist and have not been observed.

Suspensions with high microbubble concentrations e.g. between $10^9$ and $10^{10}$ bubbles/ml of relatively high stability and long storage capacity may be prepared even if the concentration of the phospholipid surfactants are kept well below the levels known in the art. Suspensions with as little as 1 µg of phospholipids per ml may be prepared as long as the amount of the surfactants used is not below that which is necessary for formation of a single monolayer of the lipids around the gas microbubbles and as long as they are produced according to one of the methods herein disclosed.

Calculations have shown that for bubble concentrations of $10^8$ bubbles/ml depending on the size distribution of the microbubbles this concentration may be as low as 1 µg/ml or 0.0001%, however, the phospholipid concentrations between 0.0002% and up to 0.01% are preferred. More preferably the concentration of the phospholipids in the stable suspensions of microbubbles of the invention is between 0.001% and 0.009%. Although further reduction of the amount of phospholipids in the suspension is possible, suspensions prepared with less than 0.0001% wt. are unstable, their total bubble count is low and their echographic response upon injection is not satisfactory. On the other hand, suspensions prepared with more than 0.01% of phospholipids upon injection do not perform better i.e. their stability and echographic response do not further improve with the concentration. Thus, the higher concentrations may only increase the probability of undesirable side effects as set out in the discussion of the prior art. It is tentatively postulated that only the segments of the surfactants which are in the lamellar or laminar form can effectively release molecules organized properly to stabilize the bubbles. This may explain why the concentration of the surfactant may be so low without impairing the stability of the gas bubbles.

The suspensions of the invention offer important advantages over the compositions of the prior art not only because of the low phospholipid content but also because the total amount of injected solutes i.e. lipids and/or synthetic polymers and other additives is between 1,000 and 50,000 times lower than heretofore. This is achieved without any loss of microbubble concentration i.e. echogenicity or stability of the product. In addition to the very low concentration of solutes, the invention provides suspensions which may contain only the microbubbles whose contribution to the echographic signal is relatively significant i.e. suspensions which are free of any microbubbles which do not actively participate in the imaging process.

Needless to say that with such low concentrations of solutes in the injectable composition of the invention probability of undesirable side effects is greatly reduced and elimination of the injected agent is significantly improved.

The microbubble suspensions with low phospholipid content of the invention may be prepared from the film forming phospholipids whose structure has been modified in a convenient manner e.g. by freeze-drying or spray-drying solutions of the crude phospholipids in a suitable solvent. Prior to formation of the suspension by dispersion in an aqueous carrier the freeze dried or spray dried phospholipid powders are contacted with air or another gas. When contacted with the aqueous carrier the powdered phospholipids whose structure has been disrupted will form lamellarized or laminarized segments which will stabilise the microbubbles of the gas dispersed therein. Conveniently, the suspensions with low phospholipid content of the invention may also be prepared with phospholipids which were lamellarized or laminarized prior to their contacting with air or another gas. Hence, contacting the phospholipids with air or another gas may be carried out when the phospholipids are in a dry powder form or in the form of a dispersion of laminarized phospholipids in the aqueous carrier.

The term lameliar or laminar form indicates that the surfactants are in the form of thin films or sheets involving one or more molecular layers. In this form, the surfactant molecules organize in structures similar to that existing in liposome vesicles. As described in WO-A-91/15244 conversion of film forming surfactants into lameliar form can easily be done by any liposome forming method for instance by high pressure homogenisation or by sonication under acoustical or ultrasonic frequencies. The conversion into lamellar form may also be performed by coating microparticles (10 $\mu$m or less) of a hydrosoluble carrier solid (NaCl, sucrose, lactose or other carbohydrates) with a phospholipid with subsequent dissolution of the coated carrier in an aqueous phase. Similarly, insoluble particles, e.g. glass or resin microbeads may be coated by moistening in a solution of a phospholipid in an organic solvent following by evaporation of the solvent. The lipid coated microbeads are thereafter contacted with an aqueous carrier phase, whereby liposomic vesicles will form in the carrier phase. Also, phospholipids can be lamellarized by heating slightly above critical temperature (Tc) and gentle stirring. The critical temperature is the temperature of gel-to-liquid transition of the phospholipids.

Practically, to produce the low phospholipid content suspensions of microbubbles according to the invention, one may start with liposome suspensions or solutions prepared by any known technique as long as the liposomic vesicles are "unloaded", i.e. they do not have encapsulated therein any foreign material but the aqueous phase of the solution itself.

The introduction of air or gas into a liposome solution can be effected by usual means, injection i.e. forcing air or gas through tiny orifices into the liposome solution, or simply dissolving the gas in the solution by applying pressure and then suddenly releasing the pressure. Another way is to agitate or sonicate the liposome solution in the presence of air or another physiologically acceptable gas. Also one can generate the formation of a gas within the solution of liposomes itself, for instance by a gas releasing chemical reaction, e.g. decomposing a dissolved carbonate or bicarbonate by acid.

When laminarized surfactants are suspended in an aqueous liquid carrier and air or another gas is introduced to provide microbubbles, it is thought that the microbubbles become progressively surrounded and stabilised by a monomolecular layer of surfactant molecules and not a bilayer as In the case of liposome vesicles. This structural rearrangement of the surfactant molecules can be activated mechanically (agitation) or thermally. The required energy is lower in the presence of cohesion releasing agents, such as Pluronic ®. On the other hand, presence of the cohesion releasing agents in the microbubble formulations reduces the natural affinity between phospholipid molecules having as a direct consequence a reduced stability of the microbubbles to external pressures (e.g. above 20–30 Torr).

As already mentioned, to prepare the low phospholipid content suspensions of the invention, in place of phospholipid solutions, one may start with dry phospholipids which may or may not be lamellarized. When lamellarized, such phospholipids can be obtained for instance by dehydrating liposomes, i.e. liposomes which have been prepared normally by means of conventional techniques in the form of aqueous solutions and thereafter dehydrated by usual means. One of the methods for dehydrating liposomes is freeze-drying (lyophilizatlon), i.e. the liposome solution, preferably containing hydrophilic compounds, is frozen and dried by evaporation (sublimation) under reduced pressure.

In another approach, non-lamellarized or non-laminarized phospholipids may be obtained by dissolving the phospholipid in an organic solvent and drying the solution without going through liposome formation. In other words, this can be done by dissolving the phospholipids in a suitable organic solvent together with a hydrophilic stabiliser substance e.g. a polymer like PVP, PVA, PEG, etc. or a compound soluble both in the organic solvent and water and freeze-drying or spray-drying the solution. Further examples of the hydrophilic stabiliser compounds soluble in water and the organic solvent are malic acid, glycolic acid, maltol and the like. Any suitable organic solvent may be used as long as its boiling point is sufficiently low and its melting point is sufficiently high to facilitate subsequent drying. Typical organic solvents would be for instance dioxane, cyclohexanol, tertiary butanol, tetrachlorodifluoro ethylene ($C_2Cl_4F_2$) or 2-methyl-2-butanol however, tertiary butanol, 2-methyl-2-butanol and $C_2Cl_4F_2$ are preferred. In this variant the criteria used for selection of the hydrophilic stabiliser is its solubility in the organic solvent of choice. The suspensions of microbubbles are produced from such powders using the same steps as with powders of the laminarized phospholipids.

Similarly, prior to effecting the freeze-drying of prelamellarized or pre-laminarized phospholipid solutions, a hydrophilic stabiliser compound is dissolved in the solution. However, here the choice of the hydrophilic stabilisers is much greater since a carbohydrate like lactose or sucrose as well as a hydrophilic polymer like dextran, starch, PVP, PVA, PEG and the like may be used. This is useful in the present invention since such hydrophilic compounds also aid in homogenising the microbubbles size distribution and enhance stability under storage. Actually making very dilute aqueous solutions (0.0001–0.01% by weight) of freeze-dried phospholipids stabilised with, for instance, a 10:1 to 1000:1 weight ratio of polyethyleneglycol to lipid enables to produce aqueous microbubbles suspensions counting $10^9$–$10^{10}$ bubbles/ml (size distribution mainly 0.5–10 μm) which are stable, without significant observable change, even when stored for prolonged periods. This is obtained by simple dissolution of the air-stored dried laminarized phospholipids without shaking or any violent agitation. The freeze-drying technique under reduced pressure is very useful because it permits, restoration of the pressure above the dried powders with any physiologically acceptable gas, i.e. nitrogen, $CO_2$, argon, methane, freons, $SF_6$, $CF_4$, etc., whereby after redispersion of the phospholipids processed under such conditions suspensions of microbubbles containing the above gases are obtained.

It has been found that the surfactants which are convenient in this invention can be selected from amphipathic compounds capable of forming stable films in the presence of water and gases. The preferred surfactants include the lecithins (phosphatidylcholine) and other phospholipids, inter alia phosphatidic acid (PA), phosphatidylinositol phosphatidylethanolamine (PE), phosphatidylserine (PS), phosphatidylglycerol (PG), cardiolipin (CL), sphingomyelins. Examples of suitable phospholipids are natural or synthetic lecithins, such as egg or soya bean lecithin, or saturated synthetic lecithins, such as, dimyristoylphosphatidylcholine, dipalmitoylphosphatidylcholine, distearoylphosphatidylcholine or diarachidoylphosphatidylcholine or unsaturated synthetic lecithins, such as dioleylphosphatidyl choline or dilinoleylphosphatidylcholine, with saturated lecithins being preferred.

Additives like cholesterol and other substances can be added to one or more of the foregoing lipids in proportions ranging from zero to 50% by weight. Such additives may include other non-phospholipid surfactants that can be used in admixture with the film forming surfactants and most of which are known. For instance, compounds like polyoxypropylene glycol and polyoxyethylene glycol as well as various copolymers thereof, phosphatldylglycerol, phosphatidic acid, dlcetylphosphate, fatty acids, ergosterol, phytosterol, sitosterol, lanosterol, tocopherol, propyl gallate, ascorbyl palmitate and butylated hydroxy-toluene. The mount of these non-film forming surfactants are usually up to 50% by weight of the total amount of surfactants but preferably between 0 and 30%. Again this means that the concentration of the various additives in the low phospholipid content suspensions of the invention are in the range of 0–0.05% which is more than one hundred times less than in the compositions known so far.

It should also be mentioned that another feature of the suspensions of the invention is a relatively "high" gas entrapping capacity of the microbubbles i.e. high ratio between the amount of the surfactant and the total amount of the entrapped gas. Hence, with suspensions in which the microbubbles have sizes in the 1 to 5 μm range, it is tentatively estimated that the weight ratio of phospholipids present at the gas bubble-liquid interface to the volume of entrapped gas under standard conditions is between 0.1 mg/ml and 100 mg/ml.

In practice all injectable compositions should also be as far as possible isotonic with blood. Hence, before injection, small amounts Of isotonic agents may also be added to the suspensions of the invention. The isotonic agents are physiological solutions commonly used in medicine and they comprise aqueous saline solution (0.9% NaCl), 2,6% glycerol solution, 5% dextrose solution, etc.

The invention further concerns a method of making stable suspensions of microbubbles according to claim 1 usable as contrast agents in ultrasonic echography. Basically, the method comprises adapting the concentration of the phospholipids in the suspension of microbubbles stabilized by said phospholipids to a selected value within the limits set forth in the claims. Usually, one will start with a microbubble suspension containing more phospholipids than the value desired and one will reduce the amount of said phospholipids relatively to the volume of gas or air entrapped in the microbubble, without substantially reducing the count of echogenerating bubbles. This can be done, for instance, by removing portions of the carrier liquid containing phospholipids not directly involved at the air/liquid interface and diluting the suspension with more fresh carrier liquid. For doing this, one may create within the suspension region (a) where the echogenerating bubbles will gather and region (b) where said bubbles are strongly diluted. Then the liquid in region (b) can be withdrawn by separation by usual means (decantation, siphoning, etc.) and a comparable volume of fresh carrier liquid is supplied for replenishment to the suspension. This operation can be repeated one or more times, whereby the content in phospholipids not directly involved in stabilizing the bubbles will be progressively reduced.

It is generally not desirable to achieve complete removal of the phospholipid molecules not present at the bubble gas/liquid interface as some unbalance from equilibrium may result, i.e. if the depletion is advanced too far, some surfactant molecules at the gas/liquid interface may be set free with consequent bubble destabilization. Experiments have shown that the concentration of phospholipids in the carrier liquid may be decreased down to within the neighborhood of the lower limit set forth in the claims without significant changes in properties and adverse effects. This means that, actually, the optimal phospholipid concentration (within the given limits) will be rather dictated by the type of application i.e. if relatively high phospholipid concentrations are admissible, the ideal concentration value will be near the upper limit of the range. On the other hand, if depending on the condition of the patient to be diagnosed, the absolute value of phospholipids must be further reduced, this can be done without adverse effects regarding microbubble count and echogenic efficiency.

An embodiment of the method comprises selecting a film forming surfactant and optionally converting It into lamellar form using one of the methods known in the art or disclosed hereinbefore. The surfactant is then contacted with air or another gas and admixed with an aqueous liquid carrier In a closed container whereby a suspension of microbubbles will form. The suspension Is allowed to stand for a while and a layer of gas filled microbubbles formed is left to rise to the top of the container. The lower part of the mother liquor is then removed and the supernatant layer of microbubbles washed with an aqueous solution saturated with the gas used in preparation of the microbubbles. This washing can be repeated several times until substantially all unused or free surfactant molecules are removed. Unused or free molecules means all surfactant molecules that do not participate In formation of the stabilizing monomolecular layer around the gas microbubbles.

In addition to providing the low phospholipid content suspensions, the washing technique offers an additional advantage in that it allows further purification of the suspensions of the invention, i.e. by removal of all or almost all microbubbles whose contribution to the echographic response of the injected suspension is relatively insignificant. The purification thus provides suspensions comprising only positively selected microbubbles, i.e. the microbubbles which upon injection will participate equally in the reflection of echographic signals. This leads to suspensions containing not only a very low concentration of phospholipids and other additives, but free from any microbubbles which do not actively participate in the imaging process.

In a variant of the method, the surfactant which optionally may be in lamellar form, Is admixed with the aqueous liquid carrier prior to contacting with air or another gas.

Figure 1:
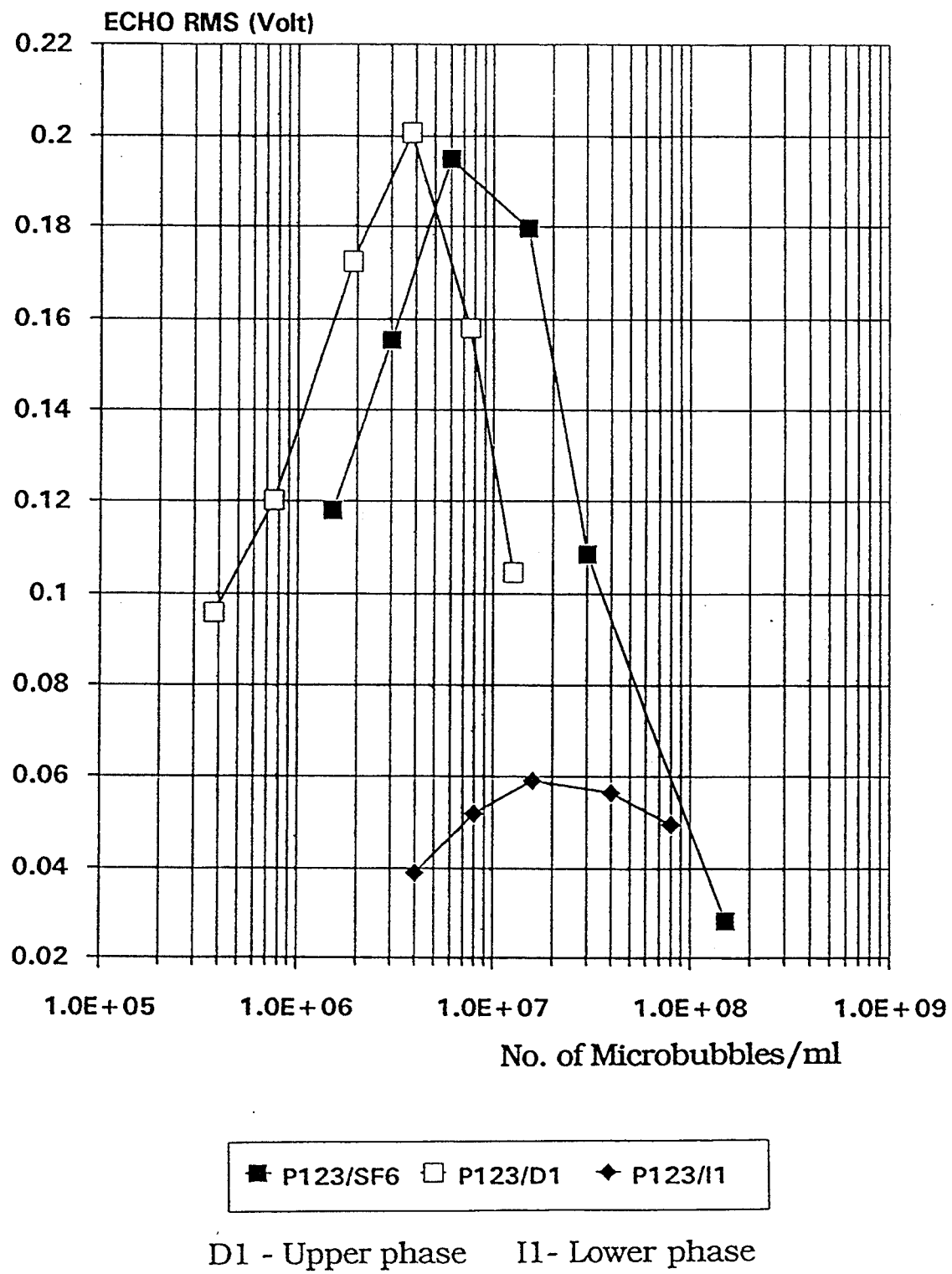
FIG. 1 is graphical presentation of echographic responses as a function of the microbubble concentration for a freshly prepared suspension according to the invention.

Suspensions and the method of making low phospholipid content suspensions of the invention will be further illustrated by the following examples:

EXAMPLE 1

Multilamellar vesicles (MLVs) were prepared by dissolving 240 mg of diarachidoylphosphatidylcholine (DAPC, from Avanti Polar Lipids) and 10 mg of dipalmitoyl-phosphatidic acid (DPPA acid form, from Avanti Polar Lipids) in 50 ml of hexane/ethanol (8/2, v/v) then evaporating the solvents to dryness in a round-bottomed flask using a rotary evaporator. The residual lipid film was dried in a vacuum dessicator. After addition of water (5 ml), the suspension was incubated at 90° C. for 30 minutes under agitation. The resulting MLVs were extruded at 85° C. through a 0.8 μm polycarbonate filter (Nuclepore ®). 2.6 ml of the resulting MLV preparation were added to 47.4 ml of a 167 mg/ml solution of dextran 10'000 MW (Fluka) in water. The resulting solution was thoroughly mixed, transferred in a 500 ml round-bottom flask, frozen at −45° C. and lyophilised under 0.1 Torr. Complete sublimation of the ice was obtained overnight. Thereafter, air pressure was restored in the evacuated container. Various amounts of the resulting powder were introduced in glass vials (see table) and the vials were closed with rubber stoppers. Vacuum was applied via a needle through the stopper and the air removed from vials. Upon evacuation of air the powder was exposed to sulfur hexafluoride gas $SF_6$.

Bubble suspensions were obtained by injecting in each vial 10 ml of a 3% glycerol solution in water (through the stopper) followed by gentle mixing. The resulting microbubble suspensions were counted using a hemacytometer. The mean bubble size (in volume) was 2.2 μm.

| Dry weight (mg/ml) | Phospholid conc. (μg per ml) | Concentration (bubbles/ml) |
|---|---|---|
| 0.5 | 8 | $9.0 \times 10^6$ |
| 1 | 16 | $1.3 \times 10^7$ |
| 5 | 81 | $7.0 \times 10^7$ |
| 10 | 161 | $1.4 \times 10^8$ |

Preparations were injected to rabbits (via the Jugular vein) as well as minipigs (via the ear vein) at a dose of 1 ml/5 kg. In vivo lo echographic measurements were performed using an Acuson XP128 ultrasound system (Acuson Corp. USA) and a 7 MHz sector transducer. The animals were anaesthetised and the transducer was positioned and then fixed in place on the left side of the chest providing a view of the right and left ventricles of the heart in the case of rabbit and a longitudinal four-chamber view in the case of the minipig. The preparation containing 0.5 mg/ml dry weight gave slight opacification of the right as well as the left ventricle in rabbits and in minipigs. The opacification, however, was superior with the 1, 5 and 10 mg/ml preparations.

EXAMPLE 2

Lyophilisates were prepared as described in Example 1 with air (instead of SF6) in the gas phase. The lyophilisates were then suspended in 0.9% saline (instead of a 3% glycerol solution). Similar bubble concentrations were obtained. However, after injection in the rabbit or the minipig the persistence of the effect was shorter e.g. 10–20 s instead of 120 s. Moreover, in the minipig the opacification of the left ventricle was poor even with the 10 mg/ml preparation.

EXAMPLE 3

MLV liposomes were prepared as described in Example 1 using 240 mg of DAPC and 10 mg of DPPA (molar ratio 95: 5). Two millilitres of this preparation were added to 20 ml of a polyethyleneglycol (PEG 2'000) solution (82.5 mg/ml). After mixing for 10 min at room temperature, the resulting solution was frozen during 5 min at −45° C. and lyophilised during 5 hours at 0.2 mbar. The powder obtained (1.6 g) was transferred into a glass vial equipped with a rubber stopper. The powder was exposed to $SF_6$ (as described in Example 1) and then dissolved in 20 ml of distilled water. The suspension obtained showed a bubble concentration of $5 \times 10^9$ bubbles per ml with a median diameter in volume of 5.5 μm. This suspension was introduced into a 20 ml syringe, the syringe was closed and left in the horizontal position for 24 hours. A white layer of bubbles could be seen on the top of solution in the syringe. Most of the liquid phase (~16–18 ml) was evacuated while the syringe was maintained in the horizontal position and an equivalent volume of fresh, $SF_6$-saturated, water was introduced. The syringe was then shaken for a while in order to homogenise the bubbles in the aqueous phase. A second decantation was performed under the same conditions after 8 hours followed by three further decantations performed in four hour intervals. The final bubble phase (batch P145) was suspended in 3 ml of distilled water. It contained $1.8 \times 10^9$ bubbles per ml with a median diameter in volume of 6.2 μm. An aliquot of this suspension (2 ml) was lyophilised during 6 hours at 0.2 mbar. The resulting powder was dissolved in 0.2 ml of tetrahydrofuran/water (9/1 v/v) and the phospholipids present in this solution were analysed by HPLC using a light scattering detector. This solution contained 0.7 mg DAPC per ml thus corresponding to 3.9 μg of phospholipids per $10^8$ bubbles. A Coulter counter analysis of the actual bubble size distribution in batch P145 gave a total surface of $4.6 \times 10^7$ gm$^2$ per $10^8$ bubbles. Assuming that one molecule of DAPC will occupy a surface of 50/Å$^2$, one can calculate that 1,3 μg of DAPC per $10^8$ bubbles would be necessary to form a monolayer of phospholipids around each bubble. The suspension P145 was than left at 4° C. and the concentration of gas bubbles measured on a regular basis. After 10 days, the product looked as good as after its preparation and still contained $1-1.2 \times 10^9$ bubbles per ml. The exceptional stability was found very surprising considering the extremely low amount of phospholipids in the suspension.

The experiment described above was repeated on a second batch of microbubbles using a shorter decantation time in order to collect preferably larger bubbles (batch P132). The median diameter in volume obtained was 8.8 μm and the total surface determined with the Coulter counter was $22 \times 10^8$ μm$^2$ per $10^8$ bubbles. The calculation showed that 6 μg DAPC for $10^8$ bubbles would be necessary to cover this bubble population with a monolayer of DAPC. The actual amount of DAPC determined by HPLC was 20 μg per $10^8$ bubbles. Taking into account the difficulty of obtaining precise estimates of the total surface of the bubble population, it appears that within the experimental error, the results obtained are consistent with coverage of the microbubbles with one phospholipid layer.

Echographic measurements performed with different washed bubble preparations showed that upon separation the lower phase gives a much weaker echographic signal than the upper phase or a freshly prepared sample. On a first sight this seemed normal as the white layer on the top of the syringe contained the majority of the gas microbubbles anyway. However, as shown in FIG. 1 the bubble count showed a surprisingly high microbubble population In the lower layer too. Only upon Coulter measurement It became apparent that the microbubbles had a size below 0.5 μm, which indicates that with small bubbles even when in high concentration, there is no adequate reflection of the ultrasound signal.

A four fold dilution of the preparation P132 in a 3% glycerol solution was injected in the minipig (0.2 ml/kg). The preparation of washed bubbles containing $2.5 \times 10^7$ bubbles per ml and 5 μg of phospholipids per ml provided excellent opacification in the left and right ventricle with outstanding endocardial border delineation. Good opacification was also obtained by injecting to a minipig an aliquot of preparation P145 (diluted in 3% glycerol) corresponding to 0.2 μg of phospholipids per kg. Contrast was even detectable in the left ventricle after injection of 0.02 μg/kg. Furthermore, in the renal artery the existence of a contrast effect could be detected by pulsed Doppler at phospholipid doses as low as 0.005 μg/kg.

It follows that as long as the laminarized phospholipids are arranged in a single monolayer around the gas microbubbles the suspensions produced will have adequate stability. Thus providing an explanation for the present unexpected finding and demonstrating that the mount of phospholipids does not have to be greater than that required for formation of a monolayer around the microbubbles present in the suspension.

EXAMPLE 4

A solution containing 48 mg of DAPC and 2 mg of DPPA in hexane/ethanol 8/2 (v/v) was prepared and the solvent evaporated to dryness (as described in Example 1). 5 mg of the resulting powder and 375 mg of polyethyleneglycol were dissolved in 5 g of tert-butanol at 60° C. The clear solution was then rapidly cooled to −45° C. and lyophilised. 80 mg of the lyophilisate was introduced in a glass vial and the powder exposed to SF$_6$ (see Example 1). A 3% glycerol solution (10 ml) was then introduced in the vial and the lyophilisate dissolved by gentle swirling. The resulting suspension had $1.5 \times 10^8$ bubbles per ml with a median diameter (in volume) of 9.5 μm. This solution was injected to a rabbit providing outstanding views of the right and left ventricle. Even a ten fold dilution of this suspension showed strong contrast enhancement.

EXAMPLE 5

The procedure of Example 4 was repeated except that the initial dissolution of the phospholipids in hexane/ethanol solution was omitted. In other words, crude phospholipids were dissolved, together with polyethylene glycol in tertiary butanol and the solution was freeze-dried; thereafter, the residue was suspended in water. Several phospholipids and combinations of phospholipids with other lipids were investigated in these experiments. In the results shown in the next table the phospholipids were dissolved in a tertiary butanol solution containing 100 mg/ml of PEG 2'000. The residues obtained after freeze drying were saturated with SF$_6$ (see Example 1), then dissolved in distilled water at a concentration of 100 mg dry weight per ml.

| Lipid mixture (weight ratio) | Conc. in tertbutanol (mg/ml) | Bubble conc. ($\times 10^9$/ml) | Median diam (μm) |
| --- | --- | --- | --- |
| DSPC | 2 | 1.3 | 10 |
| DAPC/DPPG (100/4) | 2 | 3.8 | 7 |
| DSPC/Chol (2/1) | 6 | 0.1 | 40 |
| DAPC/Plur F68 (2/1) | 6 | 0.9 | 15 |
| DAPC/Palm. ac. (60/1) | 2 | 0.6 | 11 |
| DAPC/DPPA (100/4) | 1 | 2.6 | 8 |
| DAPC/Chol/DPPA (8/1/1) | 8 | 1.2 | 19 |
| DAPC/DPPA (100/4)* | 5 | 2.4 | 18 |

Legend
DAPC = diarachidoylphosphatidyl choline
DSPC = distearoylphosphatidyl choline
DPPG = dipalmitoylphosphatidyl glycerol (acid form)
DPPA = dipalmitoylphosphatidic acid
Chol = cholesterol
Palm. ac. = palmitic acid
Plur F68 = Pluronic ®F-68
*In this experiment, CF$_4$ was used as gas instead of SF$_6$ In all cases the suspensions obtained showed high microbubble concentrations indicating that the initial conversion of phospholipids into liposomes was not necessary. These suspensions were diluted in 0.15 M NaCl and injected to minipigs as described in Example 3. In all cases outstanding opacification of the right and left ventricles as well as good delineation of the endocardial border were obtained at doses of 10-50 μg of lipids per kg body weight or less.

EXAMPLE 6

PEG-2000 (2 g), DAPC (9.6 mg) and DPPA (0.4 mg) were dissolved in 20 ml of tertiary butanol and the solution was freeze dried overnight at 0.2 mbar. The powder obtained was exposed to SF$_6$ and then dissolved in 20 ml of distilled water. The suspension containing $1.4 \times 10^9$ bubbles per ml (as determined by hemacytometry) was introduced into a 20 ml syringe, which was closed and left in horizontal position for 16 hours. A white layer of bubbles could be seen on top of the solution. The lower phase (16–18 ml) was discarded while maintaining the syringe horizontally. An equivalent volume of fresh $SF_6$-saturated distilled water was aspirated in the syringe and the bubbles were homogenised in the aqueous phase by agitation. Two different populations of microbubbles i.e. large-sized and medium-sized were obtained by repeated decantations over short periods of time, the large bubbles lo being collected after only 10–15 min of decantation and the medium sized bubbles being collected after 30–45 min. These decantations were repeated 10 times in order to obtain narrow bubble size distributions for the two types of populations and to eliminate all phospholipids which were not associated with the microbubbles. All phases containing large bubbles were pooled ("large-sized bubbles"). Similarly the fractions containing medium sized bubbles were combined ("medium-sized bubbles"). Aliquots of the two bubble populations were lyophilised and then analysed by HPLC in order to determine the mount of phospholipids present in each fraction. The large-sized bubble fraction contained $2.5 \times 10^7$ bubbles per ml with a median diameter in number of 11.3 and 13.7 µg phospholipids per $10^7$ bubbles. This result is in excellent agreement with the theoretical mount, 11.5 µg per $10^7$ bubbles, calculated assuming a monolayer of phospholipids around each bubble and a surface of 50 Å per phospholipid molecule. The medium-sized bubble fraction contained $8.8 \times 10^8$ bubbles per ml with a median diameter in number of 3.1 µm and 1.6 µg phospholipids per $10^7$ bubbles. The latter value is again in excellent agreement with the theoretical mount, 1.35 µg per $10^7$ bubbles. These results further indicate that the stability of the microbubble suspensions herein disclosed is most probably due to formation of phospholipid monolayers around the microbubbles.

We claim:

1. A method of making a suspension of air or gas filled microbubbles, said method comprising the steps of:
    selecting at least one film forming surfactant;
    converting said surfactant into a powder;
    contacting said powder with air or another gas;
    admixing said powder surfactant with an aqueous liquid carrier to form a suspension of air or gas filled microbubbles;
    introducing said suspension into a container;
    forming a layer of said microbubbles in an upper part of said container;
    separating said layer of microbubbles; and
    washing said separated microbubbles with an aqueous solution saturated with the microbubble gas.

2. The method of claim 1, in which prior to converting said surfactant into a powder, said surfactant is at least partially lamellarized.

3. The method of claim 2, in which prior to contacting said powder with air or another gas, said at least partially lamellarized surfactant is admixed with said aqueous liquid carrier.

4. The method of claim 2, in which the liquid carrier further comprises a stabilizer compound selected from the group consisting of hydrosoluble proteins, polypeptides, sugars, poly-and oligo-saccharides and hydrophilic polymers.

5. The method of claim 2, in which said conversion of said surfactant into a powder is effected by coating said surfactant onto particles of soluble or insoluble materials, leaving the coated particles for a period of time under air or a gas and admixing the coated particles with an aqueous liquid carrier.

6. The method of claim 2, in which said conversion of said surfactant into a powder is effected by sonicating or homogenizing under high pressure an aqueous solution of film forming lipids, said sonication or homogenization leading, at least in part, to the formation of liposomes.

7. The method of claim 6, in which prior to contacting said at least partially lamellarized surfactant with air or another gas, said liposome containing solution is freeze-dried.

8. The method of claim 6, in which said aqueous solution of film forming liquids also comprises viscosity enhancers or stabilizers selected from the group consisting of hydrophilic polymers and carbohydrates in weight ratio relative to said lipids of between 10:1 and 1000:1.

9. A method of making an injectable suspension of gas-filled microbubbles in an aqueous carrier liquid, said method comprising the steps off
    suspending laminarized phospholipids in an aqueous carrier liquid, said phospholipids having been in contact with said gas prior to or after suspending, under conditions such that a concentration of microbubbles is sufficient to provide an echographic response is formed in said suspension;
    allowing a portion of said phospholipids to form a stabilization layer around said bubbles; and
    thereafter depleting the aqueous carrier liquid of excess phospholipids not involved in microbubbles stabilization.

10. The method of claim 9, wherein other additives are present in said suspension of laminarized phospholipids.

11. The method of claim 9, wherein said suspension comprises at least $10^7$ microbubbles per milliliter and said stabilizers stabilize the microbubbles against collapse.

12. The method of claims 9, wherein the concentration of said phospholipids in aqueous carrier liquid is below 0.1% by weight while being equal to or above that of which the phospholipids molecules are present solely at the gas microbubble-liquid interface.

* * * * *